US012612398B2

(12) United States Patent
Wu et al.

(10) Patent No.: US 12,612,398 B2
(45) Date of Patent: Apr. 28, 2026

(54) PREPARATION METHOD FOR (R)-1,2,3,4-TETRAHYDROISOQUINOLINE-1-CARBOXYLIC ACID, DERIVATIVES THEREOF AND LEVO-PRAZIQUANTEL

(71) Applicants: TONGLI BIOMEDICAL CO., LTD., Suzhou (CN); ZHEJIANG UNIVERSITY, Hangzhou (CN)

(72) Inventors: Jianping Wu, Suzhou (CN); Lingjiao Tang, Suzhou (CN); Xiao Zhan, Suzhou (CN); Lirong Yang, Suzhou (CN); Mingxin Qian, Suzhou (CN)

(73) Assignees: Tongli Biomedical Co., Ltd., Suzhou (CN); Zhejiang University, Hangzhou (CN)

( * ) Notice: Subject to any disclaimer, the term of this patent is extended or adjusted under 35 U.S.C. 154(b) by 1051 days.

(21) Appl. No.: 17/654,974

(22) Filed: Mar. 15, 2022

(65) Prior Publication Data

US 2022/0227766 A1 Jul. 21, 2022

Related U.S. Application Data

(63) Continuation-in-part of application No. 17/654,507, filed on Mar. 11, 2022, now abandoned, which is a continuation-in-part of application No. PCT/CN2020/114338, filed on Sep. 10, 2020.

(30) Foreign Application Priority Data

Sep. 11, 2019 (CN) ........................ 201910856242.3

(51) Int. Cl.
*C07D 471/00* (2006.01)
*C07D 471/04* (2006.01)

(52) U.S. Cl.
CPC .................................. *C07D 471/04* (2013.01)

(58) Field of Classification Search
CPC .................................................... C07D 471/00
See application file for complete search history.

(56) References Cited

FOREIGN PATENT DOCUMENTS

| | | |
|---|---|---|
| CN | 103333942 A | 10/2013 |
| CN | 104327077 A | 2/2015 |
| CN | 105237532 A | 1/2016 |
| CN | 108794466 A | 11/2018 |
| CN | 109897874 A | 6/2019 |

OTHER PUBLICATIONS

International Search Report and Written Opinion issued for International Patent Application No. PCT/CN2020/114338, dated Dec. 1, 2020 in 14 pages including English translation.

Li et al., "Application of Fluidized Reactor with Recycling in the Enzymatic Synthesis of Lauroyl Maltose Ester"; Science and Technology of Food Industry, vol. 29, No. 11, Dec. 31, 2008, pp. 216-218.

Paal et al., "Directed (R)-or (S)-Selective Dynamic Kinetic Enzymatic Hydrolysis of 1,2,3,4-Tetrahydroisoquinoline-1-carboxylic Esters"; J. Org. Chem, pp. 5269-5276 (2008).

Paal et al., "Lipase-catalyzed kinetic and dynamic kinetic resolution of 1,2,3,4-tetrahydroisoquinoline-1-carboxylic acid"; Asymmetry 18, pp. 1428-1433 (2007).

Qu et al., "Study on synthesization of 7-ADCA in the fluidized-and fixed-bed reactor"; Computers and Applied Chemistry, 22 (*); pp. 605-608 (2005).

*Primary Examiner* — John S Kenyon
(74) *Attorney, Agent, or Firm* — Knobbe, Martens, Olson & Bear, LLP

(57) ABSTRACT

Preparation method for a compound as shown in formula (I) and levo-praziquantel. A racemate of ester of the compound of formula (I) is used as a substrate, and reaction is performed under the catalysis of immobilized lipase to produce the compound of formula (I); a circulating fluidized bed reactor is used, the circulating fluidized bed reactor includes an external circulation system and a reaction column, the immobilized lipase is arranged in the reaction column, the substrate solution is circulated many times between the external circulation system and the reaction column, the reaction is performed in the reaction column. The preparation of levo-praziquantel includes the described preparation steps of the formula (I). The preparation method of formula (I) can significantly improve the utilization rate of enzyme and reduce the use ratio of enzyme/substrate, and has mild reaction conditions, strong stereoselectivity, high reaction efficiency.

19 Claims, 2 Drawing Sheets

PREPARATION METHOD FOR (R)-1,2,3,4-TETRAHYDROISOQUINOLINE-1-CARBOXYLIC ACID, DERIVATIVES THEREOF AND LEVO-PRAZIQUANTEL

CROSS-REFERENCE TO RELATED APPLICATIONS

This application is a continuation in part of U.S. application Ser. No. 17/654,507, filed on Mar. 11, 2022, which is a continuation-in-part of PCT App. Serial No. PCT/CN2020/114338, having an International Filing Date of Sep. 10, 2020, which claims the benefit of priority to Chinese Patent Application No. 201910856242.3 filed on Sep. 11, 2019, and the entire disclosure thereof are hereby incorporated by reference.

TECHNICAL FIELD

The disclosure belongs to the technical field of biochemical industry, in particular relates to a preparation method of (R)-1,2,3,4-tetrahydroisoquinoline-1-carboxylic acid and its derivatives and levo-praziquantel.

BACKGROUND

In nature, tetrahydroisoquinoline alkaloids are widely distributed in plants, such as Lauraceae, Magnoliaceae, Papaveraceae, Ranunculaceae, Tranquilidae, Aristolochiaceae, etc. In 1974, Canadian scientist Kluepfel et al. isolated the tetrahydroisoquinoline compound naphthyridinomycin (NDM) from *Streptomyces lusitanus* AYB-1206 derived from soil for the first time. With the deepening of research on phytochemical components, more and more tetrahydroisoquinoline compounds have been isolated. So far, more than 60 members of the family have been reported.

In order to enrich the structural diversity of tetrahydroisoquinolines, scholars have used many classical chemical synthesis methods to modify and transform them, such as Pictect-Spengler method, Pomoanz-Fistsch method, Bischler-Napieralski method and biomimetic synthesis method. This family of compounds has a unique chemical structure and exhibits a diversity of biological activities, which has become one of the hotspots of chemists and biologists for a long time. With the deepening of research, people have discovered more and more targets of this type of compound, which have played important roles of biological activity in antibacterial, anti-tumor, anti-viral, anti-inflammatory, anti-coagulation, bronchiectasis, and central nervous system effects, and has great clinical value.

1,2,3,4-Tetrahydroisoquinoline (THIQ), as a special heterocyclic skeleton, exists in many natural alkaloids.

The carboxylic acid derivatives of THIQ are an important class of compounds, and the carboxyl substitution is 1 or 3 position. As cyclic α-amino acids with restricted conformation, they can replace the original protein amino acids and play an important role in the design of new artificial peptides. Among them, 1,2,3,4-tetrahydroisoquinoline-1-carboxylic acid (1-TIC) has been widely used in drug development and medical research. The sulfonamide hydroxime drugs synthesized by 1-TIC can effectively inhibit matrix metalloproteinase (MMP). 1-TIC can also be used to synthesize receptor antagonists of gonadotropin releasing hormone (GnRH). On the other hand, some derivatives of 1-TIC occur naturally, such as (−)-salsol-1-carboxylic acid which is found and identified in the human brain. These natural alkaloids have a wide range of therapeutic effects, such as 1-TIC derivatives containing 6,7-dimethoxy or 6,7-methylenedioxy, which can be used to synthesize inhibitors of cleavage enzymes for β-amyloid precursor protein in the treatment of Alzheimer's disease.

Among them, (R)-1-TIC is a potential building block for modified peptides or other pharmacologically active compounds. (R)-1-TIC, as a conformationally restricted analog of phenylglycine, is the structural basis for the synthesis of many biologically active peptides, such as antimicrobial peptides (AMPs) for innate immune protection. When it is used as a structurally similar substitute for phenylalanine, it can be used to synthesize farnesyltransferase inhibitors and is a new method for cancer treatment.

SUMMARY

The present disclosure is to provide a new method for preparing (R)-1,2,3,4-tetrahydroisoquinoline-1-carboxylic acid and its derivatives.

The present disclosure also provides a method for preparing levo-praziquantel, which includes the above-mentioned method for preparing (R)-1,2,3,4-tetrahydroisoquinoline-1-carboxylic acid and its derivatives.

A technical solution adopted by the present disclosure is a method for preparing the compound represented by formula (I),

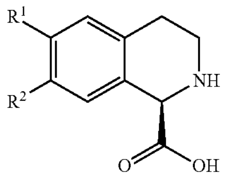

(I)

in the formula (I), $R^1$ and $R^2$ are independently selected from hydrogen, $C_1$-$C_6$ alkyl, and $C_1$-$C_6$ alkoxy, wherein the method comprises: using racemate of an ester of the compound of formula (I) as substrate and reacting under catalysis of immobilized lipase to produce the compound of formula (I), wherein, the method is performed by using a circulating fluidized bed reactor, the circulating fluidized bed reactor comprises an external circulation system and a reaction column, wherein the immobilized lipase is arranged in the reaction column, the substrate solution comprising the substrate is circulated between the external circulation system and the reaction column for many times, the reaction is carried out in the reaction column.

According to some aspects of the present disclosure, the method further comprises: after a reaction of a first batch of the substrate is completed, taking out a first batch of reaction mixture after the reaction, and then adding a second batch of the substrate to continue the reaction; after the reaction of the second batch of the substrate is completed, taking out a second batch of reaction mixture after the reaction, and then adding a third batch of the substrate to continue the reaction; after the reaction of the third batch of substrates is completed, taking out a third batch of reaction mixture, and then adding a fourth batch of the substrate to continue the reaction, and so on, to prepare n batches of reaction mixtures.

According to the present disclosure, n is greater than or equal to 5; preferably n is greater than or equal to 10; more preferably, n is greater than or equal to 15; and further preferably, n is greater than or equal to 20.

According to some specific aspects of the present disclosure, n is 10-40, preferably 15-35, and further preferably 20-30.

According to some specific aspects of the present disclosure, the substrate solution flows through the reaction column from bottom to top, which can help to maintain the immobilized lipase in a fluidized state.

According to some aspects of the present disclosure, the reaction column includes a hollow reaction tube extending in a vertical direction, a jacket covering an outside of the reaction tube (which can be used to maintain the reaction temperature in the reaction tube), and optionally, it includes a retractable piston used to control the volume of liquid inside the reaction tube, and the reaction tube is in communication with the external circulation system.

According to some aspects of the present disclosure, upper and lower ends of the reaction tube are respectively provided with filter membranes for preventing the immobilized lipase from flowing out of the reaction column.

According to some aspects of the present disclosure, the external circulation system includes a substrate container for accommodating the substrate solution, and a temperature control device for controlling the temperature of the substrate container, and optionally includes a stirring device for stirring the substrate solution, and the substrate container is in communication with the reaction column.

According to a specific aspect of the present disclosure, the temperature control device is a constant temperature water bath, the substrate container is arranged in the constant temperature water bath, the stirring device is a magnetic stirrer, and the stirring of the internal substrate solution can be achieved by placing a magnet in the substrate container.

According to a specific aspect of the present disclosure, the circulating fluidized bed reactor further includes a driving mechanism for driving the substrate solution to circulate between the external circulation system and the reaction column, and the driving mechanism includes but not be limited to peristaltic pump.

According to some aspects of the present disclosure, in the substrate solution, a concentration of the racemate of the compound of formula (I) or the racemate of a salt of the compound of formula (I) is 5-11 g/L, more preferably 9.5-10.5 g/L.

According to some aspects of the present disclosure, a concentration of the immobilized lipase in the substrate solution is 3.0-3.5 g/L, more preferably 3.15-3.45 g/L.

According to some aspects of the present disclosure, a flow rate of the substrate solution in the circulating fluidized bed reactor is 0.40-0.45 m/s, more preferably 0.41-0.43 m/s. According to some aspects of the present disclosure, a temperature of the reaction is controlled to be 25-35° C., more preferably 28-33° C., and still more preferably 29-32° C.

According to some aspects of the present disclosure, the reaction is controlled to proceed at a preset pH value, and the preset pH value is 7.8-8.2.

According to some aspects of the present disclosure, the immobilized lipase is selected from lipase QLlip-9 from Tongli Biomedical (Suzhou) Co., Ltd.

According to some specific aspects of the present disclosure, in formula (I), $R^1$ and $R^2$ are independently selected from hydrogen, methyl, ethyl, isopropyl, methoxy or ethoxy.

According to some specific aspects of the present disclosure, the ester of the compound of formula (I) is a carboxylic acid ester. According to some specific aspects of the present disclosure, the ester of the compound of formula (I) is a carboxylic acid ethyl ester. According to some specific aspects of the present disclosure, the carboxylic acid ethyl ester of the compound of formula (I) is in the form of hydrochloride salt. According to a specific aspect of the present disclosure, the ester of the compound of formula (I) is (R)-1,2,3,4-tetrahydroisoquinoline-1-carboxylate or (R)-6,7-dimethoxy-1,2,3,4-tetrahydroisoquinoline-1-carboxylate.

According to some specific aspects of the present disclosure, the compound represented by formula (I) is (R)-1,2,3,4-tetrahydroisoquinoline-1-carboxylic acid or (R)-6,7-dimethoxy-1,2,3,4-tetrahydroisoquinoline-1-carboxylic acid.

According to some specific aspects of the present disclosure, the substrate solution includes the substrate, and a pH buffering agent and/or a pH adjusting agent.

According to a specific aspect of the present disclosure, the pH buffering agent is phosphate, which can be dissolved in water to prepare a phosphate buffer solution.

According to some aspects of the present disclosure, the pH adjusting agent is preferably ammonia, alkali metal hydroxide or its aqueous solution.

According to a specific aspect of the present disclosure, the pH adjusting agent is 20 wt %-35 wt % ammonia.

The present disclosure also provides another technical solution: a preparation method of levo-praziquantel, it comprises the above-mentioned method for preparing a compound represented by formula (I), wherein $R^1$ and $R^2$ are both hydrogen, and the compound represented by formula (I) ($R^1$ and $R^2$ are both hydrogen) is used as raw material, and the levo-praziquantel is prepared through the following route:

(a) Preparation of Compound 1 (R is an Amino Protecting Group)

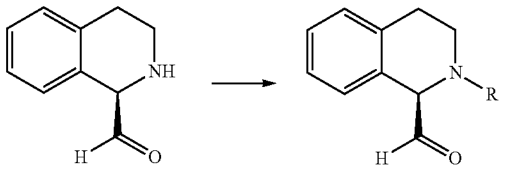

(R)-1-TIC 1

R can specifically be tert-butoxycarbonyl, benzyloxycarbonyl, fluorenylmethoxycarbonyl, allyloxycarbonyl, trichloroethoxycarbonyl, p-methoxybenzyl or benzyl, etc.;

(b) Preparation of Compound 5 from Compound 1 (i.e. Levo-Praziquantel)

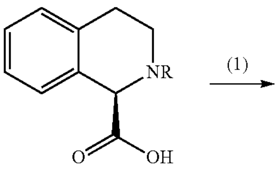

1

-continued

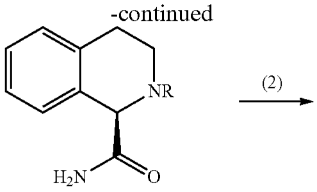

2

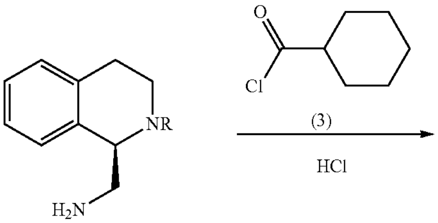

3

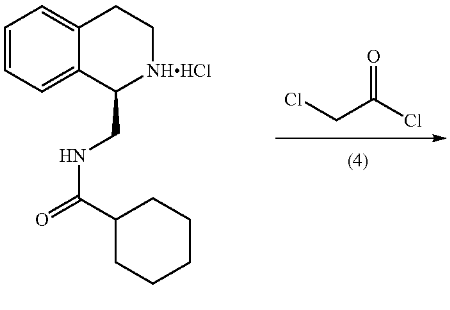

4

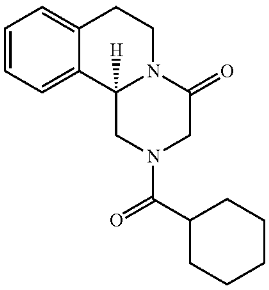

5

According to a specific aspect of the present disclosure, in step (1), firstly, compound 1 reacts with chloroformate (such as methyl chloroformate, ethyl chloroformate, isobutyl chloroformate) in the presence of pyridine and a solvent. After the reaction is completed, the precipitate is removed by filtration, and ammonia gas is passed into the reaction solution to generate compound 2. The solvent may be tetrahydrofuran. Further, step (1) can be specifically implemented as follows: adding compound 1 to tetrahydrofuran, cooling to 0-5° C., adding pyridine, and adding chloroformate (such as methyl chloroformate, ethyl chloroformate, isobutyl chloroformate) dropwise, filtering the precipitate, continuing to stir the filtrate for 1-1.5 hours, pouring in ammonia gas, stirring overnight at room temperature, adding water, extracting with ethyl acetate, drying with anhydrous sodium sulfate, filtering, concentrating, and making the residue be slurried with petroleum ether to get compound 2.

According to the present disclosure, in step (1), compound 1 can also reacts with ammonia in the presence of N,N'-carbonyldiimidazole (CDI) to obtain compound 2. According to a specific aspect, firstly, compound 1 reacts with N,N'-carbonyldiimidazole in a solvent to obtain a carbonylimidazole intermediate, and then the carbonylimidazole intermediate reacts with ammonia to generate compound 2. Further, step (1) can be implemented as follows: dissolving compound 1 in a solvent, adding N,N'-carbonyldiimidazole, stirring at room temperature for more than 5 minutes, then cooling to below 10° C., and adding ammonia water dropwise to react. Among them, stirring time at room temperature is preferably 10-30 min, and when the ammonia water is added dropwise, the temperature of the reaction system is preferably controlled to 0-5° C. The solvent is preferably tetrahydrofuran. Preferably, after obtaining the crude product, it is purified by a chromatography silica gel column, eluent is: methanol:dichloromethane=0:100-5:95. Preferably, the eluent is composed of dichloromethane and methanol with a volume ratio of 15-25:1.

Preferably, in step (2), the compound 2 is reduced by using a system of sodium borohydride/trifluoroboric acid/ether. According to a specific aspect, step (2) is specifically implemented as follows: adding compound 2 to tetrahydrofuran, adding sodium borohydride in batches under protection of argon at room temperature, heating to reflux, and adding boron trifluoride ether dropwise, continuing to stir a suspension generated for 1.5-3 hours; when gas release was not obvious and TLC detecting that the compound 2 disappeared, ending the reaction; pouring the reaction solution into HCl ice water, adjusted to pH 8.5-9.5, extracting with chloroform three times, and washing with saturated salt water, drying by anhydrous sodium sulfate, filtering, and removing the solvent to obtain a crude product of compound 3, directly used in the next reaction.

According to another specific aspect, step (2) is specifically implemented as follows: dissolving compound 2 in a solvent, adding sodium borohydride under nitrogen protection and ice bath, adding boron trifluoride ether dropwise, and keeping the temperature below 10° C. until finish adding; stirring at a temperature of 20-25° C. to react, wherein the solvent is preferably tetrahydrofuran, and the reaction time is preferably 30-42 h. Preferably, after the reaction is completed, the temperature is lowered to 0-5° C., and water is added dropwise to quench the reaction. Preferably, after the crude product is obtained, a mixed solvent composed of dichloromethane and methanol with a volume ratio of 19:1 is used to pass through the column.

Further, step (3) is implemented as follows: adding compound 3 to acetonitrile, adding pyridine and hydrochloric acid, cooling to 0-5° C., slowly adding a solution of cyclohexylformyl chloride dissolved in chloroform dropwise, after finish adding, stirring to react at room temperature. Further, step (4) is implemented as follows: adding a dichloromethane solution of compound 4 to a dichloromethane solution of chloroacetyl chloride, and then adding one selected from sodium hydroxide, potassium hydroxide, potassium tert-butoxide and organic amines, or combination thereof; after stirring for 20-40 minutes, adding benzyl triethylammonium chloride, and heating and refluxing to react until the reaction is completed. Among them, the sodium hydroxide, potassium hydroxide, potassium tert-butoxide or organic amine can be added in its original form, or can be added as an aqueous solution, and the latter is preferred. According to a specific aspect, it is preferable to add an aqueous solution of 30%-50% by weight of sodium hydroxide.

The present disclosure also provides yet another technical solution: a product of levo-praziquantel, which is prepared by the above-mentioned method and process route.

The present disclosure also provides yet another technical solution: a pharmaceutical composition for prevention and treatment of parasitic diseases, comprising an active ingredient and a pharmaceutically acceptable carrier, the active ingredient at least comprises the above-mentioned levo-praziquantel products.

DETAILED DESCRIPTION

The above solutions are further described below in conjunction with specific embodiments; it should be understood that these embodiments are used to illustrate the basic principles, main features and advantages of the present disclosure, and the present disclosure is not limited by the scope of the following embodiments. The implementation conditions can be further adjusted according to specific requirements, and the implementation conditions not specified are usually the conditions in the routine experiment.

As shown in the following examples, the method used can significantly improve the utilization rate of the enzyme and reduce the enzyme/substrate usage ratio, and has the characteristics of mild reaction conditions, strong stereoselectivity, high reaction efficiency, relatively simple process, etc., and has industrial application prospects.

According to some specific aspects of the present disclosure, the mass ratio of the immobilized lipase to the substrate is 0.001-0.8:1, preferably 0.005-0.5:1.

In the following examples, unless otherwise specified, all raw materials are commercially available or prepared by conventional methods in the art. In the following, (R)-1,2,3,4-tetrahydroisoquinoline-1-carboxylic acid is abbreviated as (R)-1-TIC; racemic substrate 1,2,3,4-tetrahydro isoquinoline-1-carboxylate (abbreviated as (±)-1) was obtained from Tongli Biomedical (Suzhou) Co., Ltd (1,2,3,4-tetrahydro-1-isoquinoline carboxylic acid ethyl ester hydrochloride), and QLlip-9 was obtained from Tongli Biomedical (Suzhou) Co., Ltd. In the following, high performance liquid chromatograph Fuli FL2200 is used to detect and analyze the target product (R)-1-TIC, and the chiral analysis column used is CHIRALPAK ZWIX(−) (0.40 cm φ×15 cm×3 μm); HPLC detection conditions: the mobile phase is methanol: acetonitrile=6:4 (containing 50 mM formic acid and 25 mM diethylamine); the flow rate is 0.4 mL·min$^{-1}$; the detection wavelength is 220 nm; the column temperature is 30° C.

Example 1

Preparation and Separation of (R)-1-TIC

Preparation of (R)-1-TIC:

Preparation of the substrate solution: the substrate solution of 10 g/L (±)-1 was prepared by using 0.1 M aqueous ammonium acetate buffer (pH=8.0), and the initial pH value of the solution was adjusted to 8.0 with 30% ammonia.

0.9 g QLlip-9 was weighted.

Figure 1:
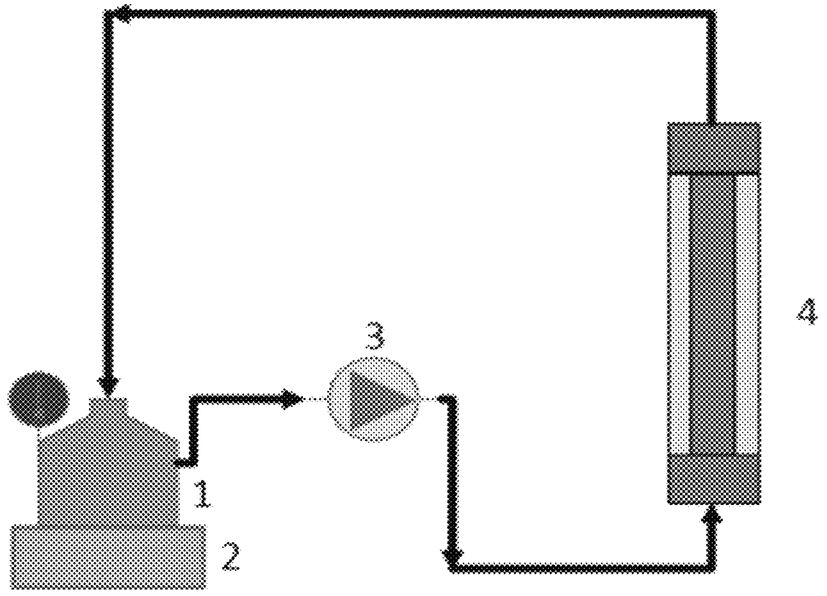
FIG. 1 is a schematic diagram of the structure of a circulating fluidized bed reactor used in the present disclosure; wherein, 1—constant temperature water bath, 2—magnetic stirrer, 3—peristaltic pump, 4—reaction column.

As shown in FIG. 1, this example provides a circulating fluidized bed reactor, comprising an external circulation system, a reaction column 4, and a peristaltic pump 3;

wherein, the external circulation system includes a substrate container for containing the substrate solution, a temperature control device for controlling the temperature of the substrate container, and a stirring device for stirring the substrate solution, wherein the substrate container is in communication with the reaction column. Specifically in the present example, the temperature control device is a constant temperature water bath 1, and the stirring device is a magnetic stirrer 2. A magnet can be placed in the substrate container to stir the internal substrate solution;

the reaction column 4 includes a hollow reaction tube extending in a vertical direction, a jacket covering the outside of the reaction tube (which can be used to maintain the reaction temperature in the reaction tube), and a retractable piston for controlling the liquid volume inside the reaction tube, The reaction tube is connected to the external circulation system. Specifically, in the present example, the reaction tube used has an inner diameter of 10 mm and a height of 30 cm. The upper and lower ends of the reaction tube are respectively provided with filter membrane for preventing QLlip-9 from flowing out of the reaction column.

The peristaltic pump 3 is used to drive the substrate solution to circulate between the external circulation system (specifically the substrate container in the present example) and the reaction column 4 (specifically the reaction tube in the present example).

Further, weighed 270 mL of the substrate solution and added it to the substrate container (continuous stirring under the action of the magnetic stirrer 2), kept it at 30° C., and added QLlip-9 (0.9 g, the concentration is about 3.33 g/L relative to the substrate solution) into the reaction tube; turned on the peristaltic pump 3, introduced the substrate solution in the substrate container into the reaction tube from bottom to top, controlled the flow rate of the substrate solution through the reaction tube to 0.42 m/s, then flowed out from the top of the reaction tube and returned to the substrate container, and the cycle repeats like this, the reaction was performed once every cycle (reaction principle: (±)-1 reacts under the catalysis of QLlip-9 to produce compound (R) of formula (I)-1-TIC), react for 12 hours, after the reaction was over, took out the reaction mixture from the substrate container and recorded it as the first batch of reaction mixture.

Then the second batch of substrate was added to the substrate container to continue the reaction. After the reaction of the second batch of substrate was completed, took out the second batch of reaction mixture after the reaction, and then added the third batch of substrate to continue. After the third batch of substrate reaction was completed, took out the third batch of reaction mixture after the reaction, and then added the fourth batch of substrate to continue the reaction, and so on, to make 20 batches of the reaction mixtures.

Treatment of Each Batch of Reaction Mixtures:

a certain amount of 1M hydrochloric acid solution was added to each batch of reaction mixtures, mixed them evenly and used them as sample solutions, then transferred all the sample solutions containing 0.5 mL reaction solution to a 25 mL volumetric flask, and used mobile phase to make constant volume and diluted.

Figure 2:
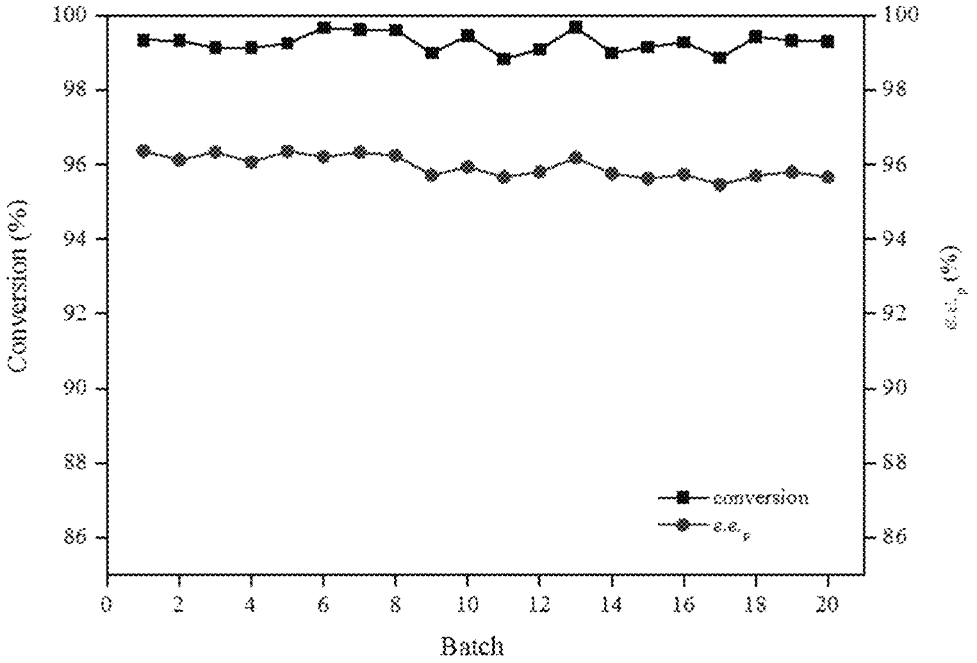
FIG. 2 shows the conversion rates and e.e.$_{p}$ values of each batch of reaction solution measured in Example 1.

Shaked well and took a certain amount of diluent, filtered it through a microporous organic filter membrane, and then injected the sample. A high performance liquid chromatography was used to determine the content of two configurations of 1,2,3,4-tetrahydroisoquinoline-1-carboxylic acid. The test results were shown in FIG. 2. All of them showed that the conversion rate was about 99% or more (conversion rate=[(initial racemic substrate concentration (g/L)−residual substrate concentration (g/L))/initial racemic substrate concentration (g/L)]×100%), $e.e._p$ was about 95.9% [$e.e._p$=(R acid product amount−S acid product amount)÷(R acid product amount+S acid product Amount)×100%], indicating that the preparation method of the present disclosure can greatly improve the utilization rate of the enzyme and significantly reduce the cost of the enzyme usage.

Separation and Purification of (R)-1-TIC:

after the reaction, the first batch of reaction mixture was filtered while warming to obtain a clear reaction solution. The reaction solution was concentrated by rotary evaporation at 60° C., a large amount of crystals were precipitated, and then fully suction filtered, and the product filter cake was separated. The filter cake is dried at 50° C., and finally dry (R)-1-TIC crystal was obtained. The separation yield was about 80% and the purity was greater than 99%.

Figure 3:
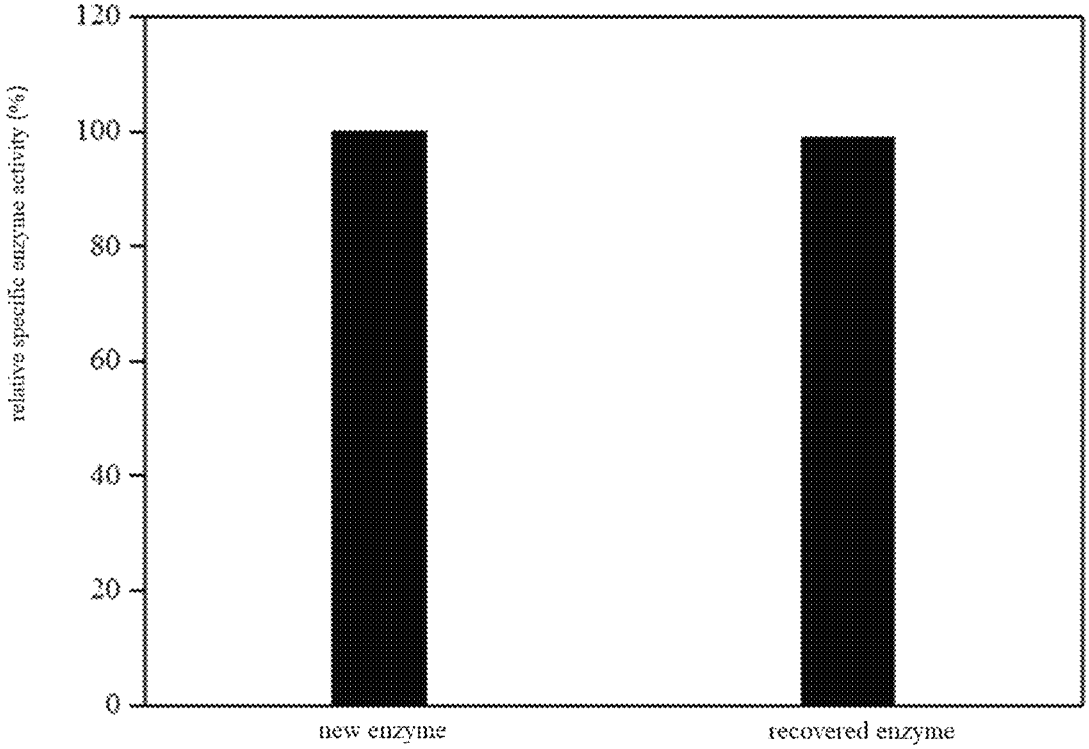
FIG. 3 shows the specific enzyme activity of the immobilized enzyme QLlip-9 after 20 batches of reuse in Example 1 and the unused new immobilized enzyme QLlip-9.

At the same time, the above-mentioned immobilized enzyme QLlip-9 that has been reused in 20 batches was recovered, and the dried recovered enzyme was obtained through vacuum freezing treatment, and the water content was calculated to be about 72%. As shown in FIG. 3, comparing the specific enzyme activity of the recovered enzyme and the new enzyme that has not undergone the catalytic reaction, the relative specific enzyme activity of the new enzyme was 100%. The result showed that the Qllip-9 has undergone 20 batches of reuse and vacuum freeze-drying. The relative enzyme activity of Qllip-9 can still be maintained at 98.86%, which proved that the enzyme has excellent operational stability and can be reused more than 20 times, which result in a significant reduction of the cost of the enzyme usage.

Example 2

Preparation and Separation of (R)-1-TIC

The preparation of (R)-1-TIC was basically the same as that in Example 1. The only differences were: 90 mL of the substrate solution was weighted, 0.3 g of QLlip-9 was added into the reaction tube, and a high performance liquid chromatography was used to determine the content of the two configurations in reaction mixture after processing 1,2,3,4-tetrahydroisoquinoline-1-carboxylic acid, the conversion rate was about 99% or more (conversion rate=[(concentration of initial racemic substrate (g/L)−residual substrate concentration (g/L))/initial racemic substrate concentration (g/L)]×100%), $e.e._p$ was about 94.3% [$e.e._p$=(R acid product amount−S acid product amount)÷(R acid product amount+S acid product amount)×100%].

The separation and purification method of (R)-1-TIC is the same as that in Example 1. After treatment, dry (R)-1-TIC crystal was obtained with a purity of more than 99%.

Example 3

Preparation and Separation of (R)-1-TIC

The preparation of (R)-1-TIC was basically the same as that in Example 1. The only differences were: 180 mL of the substrate solution was weighted, 0.6 g QLlip-9 was added into the reaction tube, and a high performance liquid chromatography was used to determine the content of the two configurations in reaction mixture after processing 1,2,3,4-tetrahydroisoquinoline-1-carboxylic acid, the conversion rate was about 99% or more (conversion rate=[(concentration of initial racemic substrate (g/L)−residual substrate concentration (g/L))/initial racemic substrate concentration (g/L)]×100%), $e.e._p$ was about 95.2% [$e.e._p$=(R acid product amount−S acid Product amount)÷(R acid product amount+S acid product amount)×100%].

The separation and purification method of (R)-1-TIC was the same as that in Example 1. After treatment, dry (R)-1-TIC crystal was obtained with a purity of more than 99%.

Example 4

Preparation and Separation of (R)-1-TIC

The preparation of (R)-1-TIC is basically the same as that in Example 1. The only differences were: 360 mL of the substrate solution was weighted, 1.2 g of QLlip-9 was added into the reaction tube, and a high performance liquid chromatography was used to determine the content of the two configurations in reaction mixture after processing 1,2,3,4-tetrahydroisoquinoline-1-carboxylic acid, the conversion rate was about 99% or more (conversion rate=[(concentration of initial racemic substrate (g/L)−residual substrate concentration (g/L))/initial racemic substrate concentration (g/L)]×100%), $e.e._p$ was about 96.0% [$e.e._p$=(R acid product amount−S acid Product amount)÷(R acid product amount+S acid product amount)×100%].

The separation and purification method of (R)-1-TIC was the same as that in Example 1. After treatment, dry (R)-1-TIC crystal was obtained with a purity of more than 99%.

Example 5

Preparation and Separation of (R)-1-TIC

The preparation of (R)-1-TIC was basically the same as that in Example 1. The only differences were that: 4 L of substrate solution was weighted, 13.4 g QLlip-9 was added into the reaction tube, and a high performance liquid chromatography was used to determine the content during the reaction 1. The contents of the two configurations of 1,2,3,4-tetrahydroisoquinoline-1-carboxylic acid were shown as follows.

| reaction time (h) | conversion rate (%) | $e.e._p$ (%) |
|---|---|---|
| 2 | 71.87 | 95.9 |
| 4 | 90.36 | 96.1 |
| 6 | 95.03 | 96.1 |
| 8 | 97.54 | 96.2 |
| 10 | 98.98 | 96.2 |
| 12 | 99.34 | 96.2 |

Figure 4:
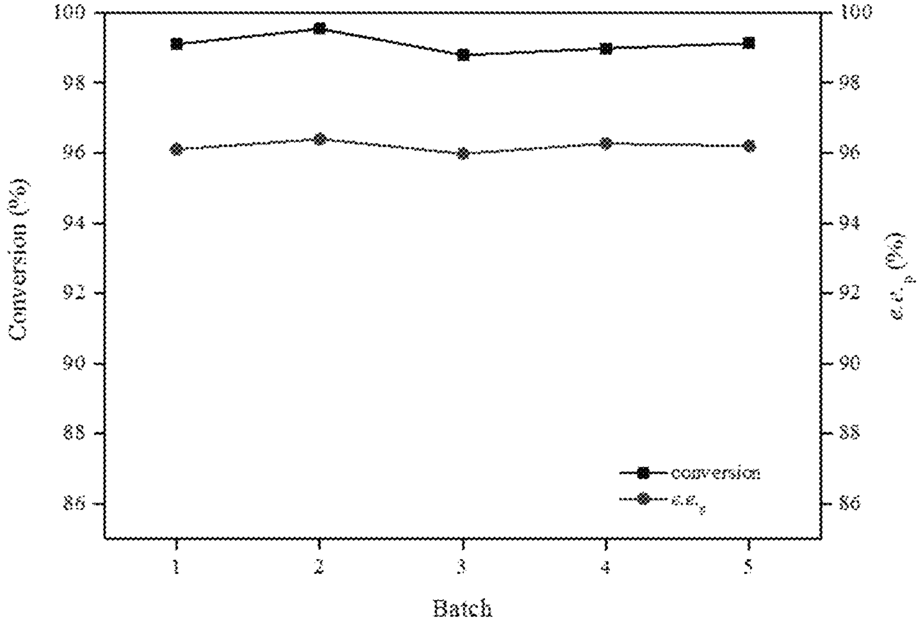
FIG. 4 shows the conversion rates and e.e.$_{p}$ values of 5 batches of reaction mixtures measured in Example 5.

In the present example, 5 batches of the reaction mixtures were repeated. Refer to FIG. 4 for the specific results, it can be seen that the conversion rates and $e.e._p$ values of the reaction mixture obtained from the 5 batches of reaction were basically the same, which not only obtained a better conversion rate and $e.e._p$ value, but also showed that after multiply repeated use of QLlip-9, its catalytic level keeps still stable, which significantly reduces the cost of enzyme usage.

Example 6

Preparation of Levo-Praziquantel

The route for (R)-1-TIC to prepare L-praziquantel was as follows:

(a) preparation of compound 1 (R is the amino protecting group Boc)

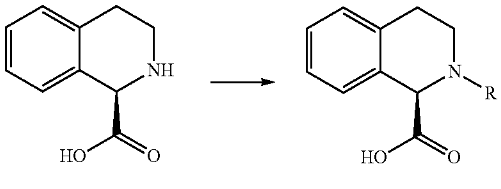

(R)-1-TIC 1

50 g (0.283 mol) 1-(R)-tetrahydroisoquinoline carboxylic acid was added to 150 mL tetrahydrofuran, cooled to 0-5° C., 120.2 g (1.13 mol) sodium carbonate dissolved in 450 mL water was added dropwise, then $Boc_2O$ (73.9 g, 0.339 mol) dissolved in 50 mL of tetrahydrofuran was added dropwise to the reaction mixture solution and stirred overnight. After the reaction, the extracted organic layer was combined and washed with saturated salt water, dried with anhydrous sodium sulfate, filtered, and concentrated in vacuo to remove the solvent. After the residue was slurried with petroleum ether, a white solid of Boc-formic acid was obtained, i.e. compound 1.

(b) Preparation of compound 5 (i.e., levo-praziquantel) from compound 1. In formulas 1 to 3, R is the same and represents the amino protecting group Boc

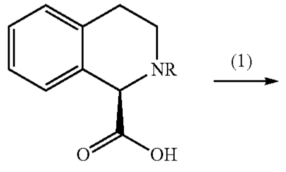

1

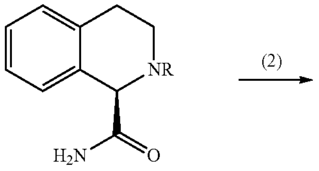

2

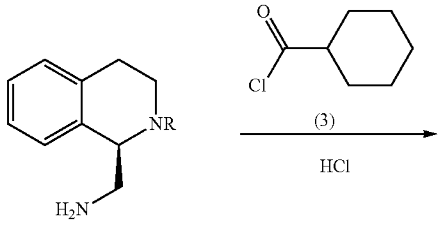

3

-continued

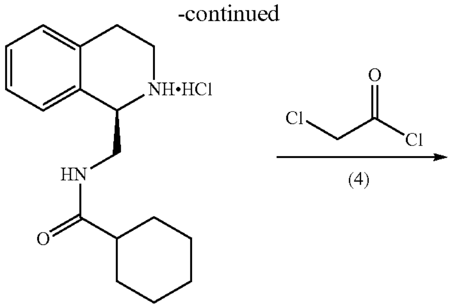

4

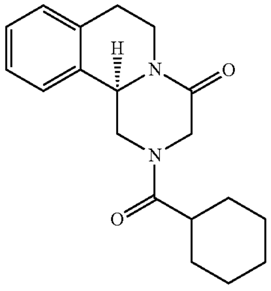

5

50 g (180 mmol) of compound 1 was added to 200 mL of tetrahydrofuran, cooled to 0° C., 28.4 g (360 mmol) of pyridine was added, 23.4 g (216 mmol) of methyl chloroformate was added dropwise, the precipitated precipitate was filtered, and the filtrate was stirred for 1 hour. Ammonia was pass into and stirred overnight. 10 mL of water was added, extracted three times with ethyl acetate, 30 mL each time, dried with anhydrous sodium sulfate, filter, and concentrate. The residue is slurried with petroleum ether to obtain Boc-formamide as a white solid, i.e. compound 2.

The NMR data of compound 2 was:

$^1H$ NMR($CDCl_3$, 400 MHz, δppm): 1.75 (s, 1H, $CH_3$), 2.78-2.86 (m, 2H, $CH_2CH_2N$), 3.58-3.76 (m, 2H, $CH_2CH_2N$), 5.3 (d, 1H, $CHCONH_2$), 6.17-6.42 (d, 1H, $CHCONH_2$), 6.61-6.86 (s, 1H, $CHCONH_2$), 7.18-7.25 (m, 4H, ArH).

35 g (126.7 mmol) of compound 2 was added to 350 mL of tetrahydrofuran. Under the protection of argon at room temperature, 27 g (633.5 mmol) of sodium borohydride was added in batches, heated to reflux, and 70 mL (633.5 mmol) of boron trifluoride ether was added dropwise. The resulting suspension was continuously stirred for 2 hours. When the gas release was not obvious, TLC detected the disappearance of the raw material amide.

The reaction solution was poured into 0.1 M HCl ice water, the pH value was adjusted to 9 with 1 N sodium hydroxide, and chloroform extracted three times with 50 mL each time. Washed with saturated brine, dried with anhydrous sodium sulfate, filter, and removed the solvent to obtain 22 g of compound 3 crude product.

22 g of compound 3 crude product (83.86 mmol) was added to 230 mL of acetonitrile, pyridine (125 ml, 125 mmol), 2 N hydrochloric acid (62.2 mL, 125 mmol) were added, cooled to 0-5° C., 19.7 g (135 mmol) of cyclohexyl formyl chloride dissolved in 71 mL chloroform was slowly added dropwise. After finish adding, the mixture was stirred and reacted overnight at room temperature, and concentrated under reduced pressure to remove the solvent. The residue was 23.1 g.

23.1 g of the residue was dissolved in 200 mL of ethyl acetate solution saturated with hydrogen chloride, stirred overnight at room temperature, and the solvent was removed by rotary evaporation. The residue was recrystallized with methanol. A white solid precipitated out and dried under vacuum to obtain a white solid of cyclohexanol formamide hydrochloride, i.e. compound 4.

The white solid of cyclohexanol formamide hydrochloride (22 g, 71.23 mmol, compound 4) was dissolved in 90 mL of dichloromethane, and chloroacetyl chloride (8.29 g, 71.23 mmol) dissolved in 30 mL of dichloromethane was added, followed by the addition of 50% NaOH solution (25.32 mL). After stirring for 30 minutes, benzyl triethyl ammonium chloride (TEBAC, 1.64 g, 7.12 mmol) was added and heated to reflux for 2 hours. After the reaction, 125 mL of water was added and extracted with dichloromethane. The combined organic phase was washed twice with water, washed with 5% hydrochloric acid solution, then washed with saturated salt water, and dried with anhydrous sodium sulfate. After evaporating the solvent, the residue was subjected to silica gel column chromatography with an eluent of PE/EA=20:1~5:1, and the peak of the target product was collected and concentrated. The obtained concentrate was dissolved in ethyl acetate and heated to dissolve, slowly cooled to precipitate crystals, filtered and dried to obtain a white solid of levo-praziquantel (compound 5) with a purity of 99.16% and 100% ee.

The NMR data of levo-praziquantel crystal form are as follows:

$^1$H NMR (300 MHz, DMSO-d6): δ1.26-1.30 (m, 3H), 1.46-1.63 (m, 3H), 1.72-1.88 (m, 5H), 2.43-2.56 (m, 1H), 2.77-2.87 (m, 2H), 2.90-3.25 (m, 2H), 3.84-4.10 (m, 1H), 4.35-4.49 (m, 1H), 4.79-4.87 (m, 2H), 5.15-5.18 (d, 1H), 7.17-7.19 (d, 2H), 7.24-7.28 (d, 2H).

From above examples, it can be seen that the method used offers not only high conversion rate (up to 99%), but also yield product enantiomeric excess ($e.e._p$) value (up to 96%), moreover, it significantly improves the utilization rate of immobilized lipase (recycling rate can reach 20 even more than 30 times without manual separation); furthermore, the enzyme/substrate usage ratio is significantly reduced, which greatly saves the cost of enzyme use (cost can be reduced by 30 times or even 35 times), which is conducive to industrial application.

The above-mentioned embodiments are only to illustrate the technical concept and characteristics of the present disclosure, and their purpose is to enable those familiar with the technology to understand the content of the present disclosure and implement them accordingly and should not limit the protection scope of the present disclosure. All equivalent changes or modifications made according to the present disclosure should be covered by the protection scope of the present disclosure.

We claim:

1. A method for preparing a compound represented by formula (I),

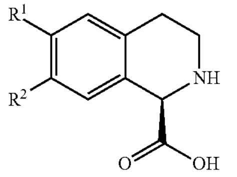

(I)

wherein, in the formula (I), $R^1$ and $R^2$ are independently selected from hydrogen, $C_1$-$C_6$ alkyl, and $C_1$-$C_6$ alkoxy, wherein the method comprises:

using racemate of an ester of the compound of formula (I) as substrate and reacting under catalysis of immobilized lipase to produce the compound of formula (I), wherein the method is performed by using a circulating fluidized bed reactor, the circulating fluidized bed reactor comprises an external circulation system and a reaction column, wherein the immobilized lipase is arranged in the reaction column, the method comprises circulating a substrate solution comprising the substrate between the external circulation system and the reaction column;

conducting a reaction of a first batch of the substrate;

taking out the first batch of reaction mixture after the completion of the reaction of the first batch of the substrate, and then adding a second batch of the substrate to continue the reaction;

taking out the second batch of reaction mixture after the completion of the reaction of the second batch of the substrate, and then adding a third batch of the substrate to continue the reaction, wherein taking out a third batch of reaction mixture after the completion of the reaction of the third batch of the substrate, and then adding a fourth batch of the substrate to continue the reaction, and so on, to prepare n batches of reaction mixtures in total, the n is greater than or equal to 5, wherein in the substrate solution, concentration of the racemate of the ester of the compound of formula (I) is 9.5-10.5 g/L, wherein addition amount ratio of the immobilized lipase to the substrate solution is 2.0-3.5 g/L, and wherein flow rate of the substrate solution in the circulating fluidized bed reactor is 0.40-0.45 m/s; and making the substrate solution flow through the reaction column from bottom to top, wherein the reaction column comprises a hollow reaction tube extending in an up and down direction, and a jacket covering an outside of the hollow reaction tube, the reaction column optionally comprises a telescopic piston for controlling a volume of liquid inside the hollow reaction tube, and the hollow reaction tube is in communication with the external circulation system, and wherein upper and lower ends of the hollow reaction tube are respectively provided with a filter membrane for preventing the immobilized lipase from flowing out of the reaction column.

2. The method for preparing the compound represented by formula (I) according to claim 1, wherein, the n is greater than or equal to 10.

3. The method for preparing the compound represented by formula (I) according to claim 1, wherein, the n is 10-40.

4. The method for preparing the compound represented by formula (I) according to claim 1, wherein, the external circulation system comprises a substrate container for accommodating the substrate solution, and a temperature control device for controlling temperature of the substrate container, the external circulation system optionally comprises a stirring device for stirring the substrate solution, and the substrate container is connected with the reaction column.

5. The method for preparing the compound represented by formula (I) according to claim 1, wherein, addition amount ratio of the immobilized lipase to the substrate solution is 3.15-3.45 g/L.

6. The method for preparing the compound represented by formula (I) according to claim 1, wherein, flow rate of the substrate solution in the circulating fluidized bed reactor is 0.41-0.43 m/s.

7. The method for preparing the compound represented by formula (I) according to claim 1, wherein, temperature of the reaction is controlled to be 25-35° C.

8. The method for preparing the compound represented by formula (I) according to claim 1, wherein, the reaction is performed under a preset pH, and a value of the preset pH is 7.8-8.2.

9. The method for preparing the compound represented by formula (I) according to claim 1, wherein, in formula (I), $R^1$ and $R^2$ are independently selected from hydrogen, methyl, ethyl, isopropyl, methoxy and ethoxy, the ester of the compound of formula (I) is a carboxylic acid ester.

10. The method for preparing the compound represented by formula (I) according to claim 1, wherein, the compound represented by formula (I) is (R)-1,2,3,4-tetrahydroisoquinoline-1-carboxylic acid or (R)-6,7-dimethoxy-1,2,3,4-tetrahydroisoquinoline-1-carboxylic acid.

11. The method for preparing the compound represented by formula (I) according to claim 1, wherein, the substrate solution comprises the substrate, and a pH buffering agent and/or a pH adjusting agent.

12. The method for preparing the compound represented by formula (I) according to claim 1, wherein the external circulation system comprises a substrate container for containing the substrate solution, and a temperature control device for controlling temperature of the substrate container, and optionally a stirring device for stirring the substrate solution, the substrate container is in communication with the hollow reaction tube, and wherein the substrate solution comprises the substrate, and a pH buffering agent and/or a pH adjusting agent, and has a pH value of 7.8-8.2.

13. A preparation method of levo-praziquantel comprising:

preparing the compound represented by formula (I) according to claim 1;

reacting the compound represented by formula (I) with an amino protecting agent to produce compound 1;

reacting the compound 1 with ammonia to produce compound 2;

reacting the compound 2 with a reducing agent to produce compound 3;

reacting the compound 3 with cyclohexylformyl chloride and hydrochloric acid to produce compound 4; and reacting the compound 4 with chloroacetyl chloride to produce compound 5, wherein, in formula (I), $R^1$ and $R^2$ are both hydrogen, wherein a reaction schematic diagram of the preparation method comprises:

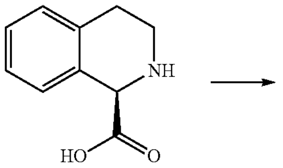

(1)

-continued

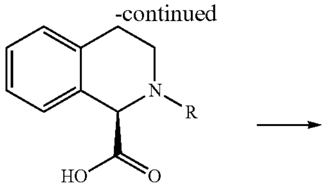

1

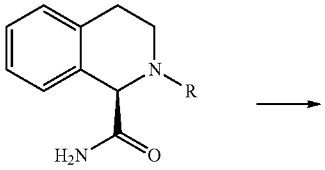

2

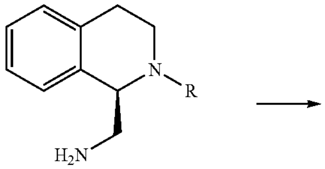

3

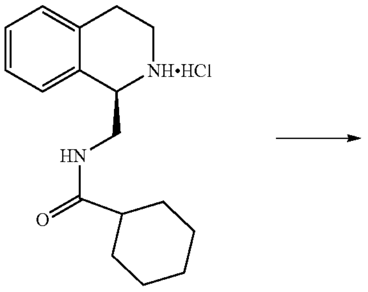

4

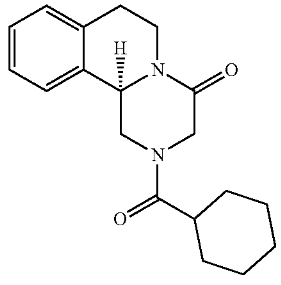

5 wherein, in the reaction schematic diagram and in the compounds 1, 2 and 3, R is an amino protecting group.

14. The method for preparing the compound represented by formula (I) according to claim 1, wherein, the n is greater than or equal to 15.

15. The method for preparing the compound represented by formula (I) according to claim 1, wherein, the n is greater than or equal to 20.

16. The method for preparing the compound represented by formula (I) according to claim 1, wherein, the n is 15-35.

17. The method for preparing the compound represented by formula (I) according to claim 1, wherein, the n is 20-30.

18. The method for preparing the compound represented by formula (I) according to claim 1, wherein, temperature of the reaction is controlled to be 28-33° C.

19. The method for preparing the compound represented by formula (I) according to claim 1, wherein, temperature of the reaction is controlled to be 29-32° C.

* * * * *